United States Patent [19]

Schönafinger et al.

[11] Patent Number: 5,389,655
[45] Date of Patent: Feb. 14, 1995

[54] PHENYLFUROXANS

[75] Inventors: Karl Schönafinger, Alzenau; Helmut Bohn, Schöneck, both of Germany

[73] Assignee: Cassella AG, Frankfurt am Main

[21] Appl. No.: 65,547

[22] Filed: May 20, 1993

[30] Foreign Application Priority Data

May 29, 1992 [DE] Germany ............................ 4217794

[51] Int. Cl.⁶ .................... C07D 413/04; A61K 31/41
[52] U.S. Cl. .................... 514/364; 548/125; 546/277
[58] Field of Search ............ 548/129; 514/364; 546/277

[56] References Cited

U.S. PATENT DOCUMENTS

| | | | |
|---|---|---|---|
| 4,356,178 | 10/1982 | Schonafinger et al. | 424/248 |
| 4,416,893 | 11/1983 | Schoenafinger | 548/125 |

FOREIGN PATENT DOCUMENTS

| | | | |
|---|---|---|---|
| 1173034 | 8/1984 | Canada | 260/2465 |
| A498137 | 12/1970 | China | C07D 85/56 |
| A498856 | 12/1970 | China | C07D 85/56 |
| 75141 | 3/1983 | European Pat. Off. | C07D 271/08 |
| 497122 | 7/1992 | European Pat. Off. | 548/125 |

OTHER PUBLICATIONS

Calvino, Fur. J. Med. Chem.–Chim. Ther 15 487 (1980).
Potts, Comprehensive Heterocyclic Chemistry vol. 6 p. 406 (1984).
Helv. Chim. Acta 53 (1970), pp. 1883–1892.
J. Heterocycl. Chem. 19 (1982), pp. 427–430.
Liebigs Ann. Chem., 1990, pp. 335–338.
Ann. Chim. (Rome) 1968, vol. 58, pp. 200–212.
"Nitric Oxide" by Burnett et al., Science, vol. 257, pp. 401–403.
"Biological Roles of Nitric Oxide" by Snyder et al., Nedicine, Scientific American, May 1992, pp. 22–29.
Chemical Abstract, vol. 105 (1986), Abstract No. 114403a.

Primary Examiner—Robert Gerstl

[57] ABSTRACT

The present invention relates to phenylfuroxans of the general formula I

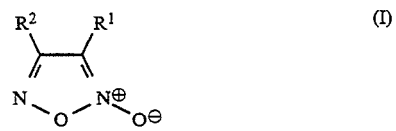

in which one of the radicals $R^1$ and $R^2$ represents phenyl and the other represents

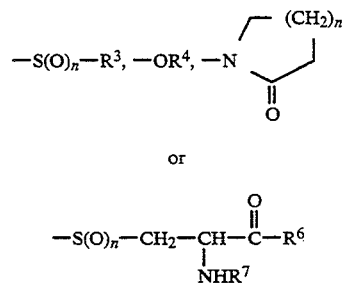

where $R^3$, $R^4$ and n are defined as indicated in claim 1, processes for their preparation and their use.

9 Claims, No Drawings

PHENYLFUROXANS

The present invention relates to substituted phenylfuroxans, processes for their preparation and their use.

A number of compounds from the phenylfuroxan class are already known and described, for example, in Helv. Chim. Acta 53 (1970), 1883–1892 and J. Het. Chem. 19 (1982) 2, 427–430.

The present invention relates to phenylfuroxans of the general formula I

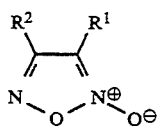

in which one of the radicals $R^1$ and $R^2$ represents phenyl and the other represents

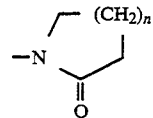

or $$-S(O)_n-CH_2-CH-\underset{NHR^7}{\overset{\overset{O}{\|}}{C}}-R^6$$

where $R^3$ denotes $(C_1-C_6)$-alkyl, $(C_5-C_7)$-cycloalkyl, $(C_7-C_{10})$-aralkyl, $(C_3-C_7)$-alkenyl, —$(CH_2)_m R^5$ or —$(CH_2)_n$—CO—$R^6$;

$R^4$ denotes $(C_3-C_6)$-alkyl, $(C_5-C_7)$-cycloalkyl, $(C_3-C_7)$-alkenyl, —$(CH_2)_n$—Het, —$(CH_2)_m$—$R^5$ or $(C_7-C_{10})$-aralkyl;

$R^5$ denotes hydroxyl, alkoxy, alkylamino, dialkylamino or N-alkyl-N-aralkylamino;

$R^6$ denotes hydroxyl, amino, alkylamino, dialkylamino or $OR^{3'}$, where $R^{3'}$, with the exception of —$(CH_2)_n$—CO—$R^6$, is defined as $R^3$;

$R^7$ denotes hydrogen, $(C_1-C_6)$-alkyl or $(C_2-C_7)$-alkylcarbonyl;

Het represents a heterocycle; and n represents 0, 1 or 2 and m represents 2, 3 or 4, and their pharmacologically acceptable acid addition compounds.

The said alkyl groups can be straight-chain or branched. Examples are methyl, ethyl, n-propyl, i-propyl, n-butyl, i-butyl, sec-butyl, tert-butyl, pentyl or hexyl. The same applies to alkoxy, alkylamino or dialkylamino groups.

$(C_5-C_7)$-Cycloalkyl representing $R^3$ or $R^4$ preferably denotes cyclopentyl or cyclohexyl.

Alkoxy representing $R^5$ is preferably $(C_1-C_6)$-alkoxy. Alkylamino or dialkylamino representing $R^5$ and $R^6$ and N-alkyl-N-aralkylamino representing $R^5$ preferably have 1 to 6 carbon atoms per alkyl radical.

$(C_2-C_7)$-Alkylcarbonyl representing $R^7$ is preferably acetyl or propionyl.

$(C_7-C_{10})$-Aralkyl representing $R^3$ or $R^4$ is in particular benzyl or phenylethyl.

$(C_3-C_7)$-Alkenyl representing $R^3$ or $R^4$ is in particular allyl.

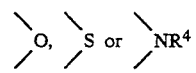

representing $R^1$ or $R^2$ preferably denotes 2-oxopyrrolidin-1-yl.

A heterocycle representing Her is preferably 5- to 7-membered and can be aliphatic or aromatic. Moreover, it can also be substituted. In particular, it contains $$\diagdown\!\!\!\diagup\!\!\!\mathrm{O}, \quad \diagdown\!\!\!\diagup\!\!\!\mathrm{S} \quad \text{or} \quad \diagdown\!\!\!\diagup\!\!\!\mathrm{NR^4}$$

as hetero members. If the heterocycle has 2 hetero members, these can be identical or different. A nitrogen-containing heterocycle can also be bonded via the hetero N atom; besides the first nitrogen atom which brings about the bond, it can then additionally contain any of the abovementioned hetero members desired. Examples of heterocyclic radicals of this type which are bonded via a hetero N atom are the N-pyrrolidine radical or the N-thiomorpholine radical.

Aromatic heterocyclic radicals are those which, as a result of conjugation of double bonds, if appropriate having free electron pairs, within the ring, can form mesomeric limiting structures, such as, for example, the thienyl radical or the pyrazolyl radical. Aliphatic heterocyclic radicals contain only isolated double bonds or no double bonds at all, such as, for example, the pyrrolidine radical, the piperidine radical, the morpholine radical or the perhydrothiazepine radical. Of the heterocycles which contain two hetero members, those are preferred which have at least one nitrogen-containing hetero member.

Examples of heterocycles from which the radicals Het are derived are: thiophene, di- or tetrahydrothiophene, pyrrole, pyrroline, pyrrolidine, pyridine, dihydropyridine, piperidine, pyran, perhydropyran, oxepine, thiepine, azepine, perhydrooxepine, perhydrothiepine, perhydroazepine, imidazole, imidazoline, imidazolidine, oxazole, oxazoline, oxazolidine, thiazole, thiazoline, thiazolidine, pyrimidine, pyridazine, pyrazine, piperazine, morpholine, thiomorpholine, diazepine, oxazepine, thiazepine, perhydrodiazepine, -oxazepine and thiazepine.

Particularly preferred radicals Het are derived from pyrrole, pyrrolidine, imidazole, thiazole, thiazolidine, perhydrothiazepine and pyridine.

In the hetero members of the formula

$R^4$ represents hydrogen, alkyl having 1 to 4, preferably 1 or 2, C atoms or alkoxycarbonyl having 1 to 4 C atoms in the alkoxy group.

The heterocyclic radicals can also carry on one of the ring carbon atoms a substituent such as, for example, a carboxyl group, a formyl group, alkoxycarbonyl having 1 to 4, preferably 1 or 2, C atoms in the alkoxy group or, preferably, an alkyl group having 1 to 4, preferably 1 or 2, C atoms.

Aliphatic heterocyclic radicals, in particular those which are derived from nitrogen heterocycles, can also have on one ring carbon atom, preferably a ring carbon atom adjacent to the nitrogen-containing hereto member, a keto function, a double-bonded oxygen atom. This can also be present in its tautomeric form.

The heterocyclic radicals can optionally also be fused to a benzene ring which, for its part, can optionally be substituted by alkyl having 1 to 4, preferably 1 or 2, C atoms, or alkoxy having 1 to 4, preferably 1 or 2, C atoms. Examples of condensed heterocycles of this type are indole and quinazoline.

Preferred compounds of the general formula I are those in which $R^2$ denotes phenyl and $R^1$ represents $-S(O)_n-R^3$ or $-OR^4$.

Particularly preferred compounds of the general formula I are those in which $R^1$ denotes phenyl.

Very particularly preferred compounds of the general formula I are those in which $R^1$ denotes phenyl and $R^2$ denotes $-S(O)_n R^3$ or $-OR^4$.

The compounds of the general formula I can be prepared, for example, by oxidising a compound of the general formula II

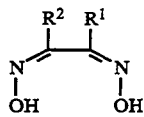

in which $R^1$ and $R^2$ are defined as indicated above.

Oxidising agents which can be employed in this oxidation are conventional reagents such as, for example, halogens, alkali metal hypochlorites, iron(III) salts, such as, for example, potassium ferrocyanide or nitrous gases, such as, for example, $N_2O_4$. The reaction is preferably carried out in a solvent, such as, for example, water, an alcohol, an ether, ethyl acetate, methylene chloride, benzene, toluene or chlorobenzene, at temperatures from $-10°$ C. to $50°$ C., preferably from $-5°$ C. to $25°$ C.

In the said oxidation, the compounds of the general formula I are as a rule obtained in the form of isomer mixtures. These can be separated, however, by known methods such as recrystallisation or chromatography. Isomer mixtures are also obtained when a pure isomer is heated without solvent or dissolved in an inert solvent to temperatures of 50° to 200° C. or photolysed at 0° to 50° C. By separation of the mixture thus obtained, it is thus possible to convert one isomer into the other.

The compounds of the general formula II can be obtained from the compounds of the general formula IIa

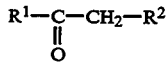

in a manner known per se by nitrosation and subsequent reaction with hydroxylamine.

A preferred process for the preparation of the compounds of the general formula I consists in reacting a compound of the general formula III

in which one of the radicals $R^7$ and $R^8$ represents phenyl and the other represents a nucleofugic group, with a compound

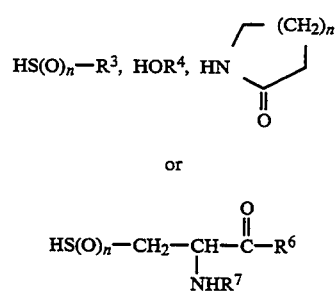

in which $R^3$, $R^4$, $R^6$, $R^7$ and n are defined as indicated above.

Preferred nucleofungic groups are, for example, halogen and in particular nitro.

Advantageously, the reaction is carried out in the presence of a base which neutralises the resulting acids. Preferred bases are alkali metal carbonates, such as sodium hydrogencarbonate or potassium hydrogencarbonate or sodium carbonate or potassium carbonate, alkali metal hydroxides, such as sodium hydroxide, potassium hydroxide or lithium hydroxide, alkali metal alkoxides, such as sodium methoxide or potassium methoxide, sodium ethoxide or potassium ethoxide or potassium tert-butoxide, alkali metal hydrides, such as sodium hydride or potassium hydride, alkali metal amides, such as sodium amide or lithium diisopropylamide or organic bases such as pyridine or triethylamine. These bases are preferably employed in molar amounts. Suitable solvents are, for example, ether, THF, alcohols, toluene, DMF and DMSO. The temperatures are 0° to 100° C., preferably 0° to 50° C.

If desired, the compounds of the general formula I according to the invention prepared by one of the abovementioned processes can be converted into further compounds of the general formula I according to the invention by modification of the substituents.

For example, the side chain $-SR^3$ can be converted with the aid of hydrogen peroxide or peracids in a manner known per se into side chains $-S(O)R^3$ or $-S(O)_2R^3$. $-(CH_2)_n-CO-OR^{3'}$ radicals representing $R^3$ can furthermore be converted by reaction with corresponding amines into $-(CH_2)_n-CO-R^6$ radicals, in which $R^6$ denotes amino, alkylamino, dialkylamino, or into $-(CH_2)_n-COOH$ radicals by hydrolysis.

The synthesis of the compounds of the general formula III is known per se and described, for example, in Izv. Akad. Nauk SSR, Ser. Khim 1990, 7, 1620–1622; Bull. Chem. Soc. Jpn. 63, 1843–1844 (1990); and in Gazz. Chim. Ital. 62 127–131 (1932).

Besides the compounds described in the examples, the following compounds according to the invention can also be prepared according to above preparation processes:

3-Phenyl-4-methylmercapto-1,2,5-oxadiazole-2-oxide
3-Phenyl-4-propylmercapto-1,2,5-oxadiazole-2-oxide
3-Phenyl-4-isopropylmercapto-1,2,5-oxadiazole-2-oxide
3-Phenyl-4-isobutylmercapto-1,2,5-oxadiazole-2-oxide
3-Phenyl-4-pentylmercapto-1,2,5-oxadiazole-2-oxide
3-Phenyl-4-hexylmercapto-1,2,5-oxadiazole-2-oxide
3-Phenyl-4-neopentylmercapto-1,2,5-oxadiazole-2-oxide
3-Phenyl-4-methylsulphonyl-1,2,5-oxadiazole-2-oxide
3-Phenyl-4-ethylsulphonyl-1,2,5-oxadiazole-2-oxide
3-Phenyl-4-isopropylsulphonyl-1,2,5-oxadiazole-2-oxide
3-Phenyl-4-hexylsulphonyl-1,2,5-oxadiazole-2-oxide
3-Phenyl-4-methylsulphinyl-1,2,5-oxadiazole-2-oxide
3-Phenyl-4-butylsulphinyl-1,2,5-oxadiazole-2-oxide
3-Phenyl-4-propylsulphinyl-1,2,5-oxadiazole-2-oxide
3-Phenyl-4-allylsulphinyl-1,2,5-oxadiazole-2-oxide
3-Phenyl-4-allylsulphonyl-1,2,5-oxadiazole-2-oxide
3-Phenyl-4-benzylmercapto-1,2,5-oxadiazole-2-oxide
3-Phenyl-4-phenylethylmercapto-1,2,5-oxadiazole-2-oxide
3-Phenyl-4-methoxyethylmercapto-1,2,5-oxadiazole-2-oxide
3-Phenyl-4-benzylsulphinyl-1,2,5-oxadiazole-2-oxide
3-Phenyl-4-methoxypropylsulphonyl-1,2,5-oxadiazole-2-oxide
3-Phenyl-4-benzylsulphonyl-1,2,5-oxadiazole-2-oxide
3-Phenyl-4-diisopropylaminoethylsulphonyl-1,2,5-oxadiazole-2-oxide
3-Phenyl-4-dimethylaminoethylmercapto-1,2,5-oxadiazole-2-oxide
3-Phenyl-4-isopropoxyethylsulphonyl-1,2,5-oxadiazole-2-oxide
3-Phenyl-4-cyclohexylsulphonyl-1,2,5-oxadiazole-2-oxide
3-Phenyl-4-methylaminoethylmercapto-1,2,5-oxadiazole-2-oxide
3-Phenyl-4-isopropylaminoethylsulphonyl-1,2,5-oxadiazole-2-oxide
3-Phenyl-4-cyclopentylsulphonyl-1,2,5-oxadiazole-2-oxide
3-Phenyl-4-phenylethoxy-1,2,5-oxadiazole-2-oxide
3-Phenyl-4-benzyloxy-1,2,5-oxadiazole-2-oxide
3-Phenyl-4-ethoxyethoxy-1,2,5-oxadiazole-2-oxide
3-Phenyl-4-methoxypropoxy-1,2,5-oxadiazole-2-oxide
3-Phenyl-4-butoxy-1,2,5-oxadiazole-2-oxide
3-Phenyl-4-cyclohexyloxy-1,2,5-oxadiazole-2-oxide
3-Phenyl-4-cyclopentoxy-1,2,5-oxadiazole-2-oxide
3-Phenyl-4-allyloxy-1,2,5-oxadiazole-2-oxide
3-Phenyl-4-methylaminoethoxy-1,2,5-oxadiazole-2-oxide
3-Phenyl-4-methoxycarbonylethylmercapto-1,2,5-oxadiazole-2-oxide
3-Phenyl-4-ethoxycarbonylethylsulphonyl-1,2,5-oxadiazole-2-oxide
3-Phenyl-4-butoxyethoxy-1,2,5-oxadiazole-2-oxide
3-Phenyl-4-(2-oxopiperidino)-1,2,5-oxadiazole-2-oxide
and the corresponding compounds in which the substituents in the 3- and 4-position are exchanged, i.e., for example, 4-phenyl-3-methylmercapto-1,2,5-oxadiazole-2-oxide, etc.

Compounds of the general formula I according to the invention which contain a basic group can form salts with inorganic or organic acids. Suitable acids for the formation of pharmacologically acceptable acid addition salts are, for example: hydrogen chloride, hydrogen bromide, naphthalenedisulphonic acids, in particular 1,5-naphthalenedisulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. The acid addition salts can be prepared in the customary manner by combination of the components, expediently in a suitable solvent or diluent.

The compounds of the general formula I and their pharmacologically acceptable acid addition salts have useful pharmacological properties. In the guinea-pig potassium-depolarised pulmonary artery model, they lead at low concentrations to a long-lasting relaxation. This action can be inhibited with oxyhaemoglobin, which points to an NO-mediated mechanism. As a guanylate cyclase activator, nitrogen monoxide leads to an increase in cyclic guanosine monophosphate, which causes a relaxation in the smooth muscle and antiadhesive and antiaggregatory actions in the blood platelets. Nitrogen monoxide is additionally crucially involved in learning processes, in the regulation of the kidney function, in immune defence, in septic shock and in erectile dysfunctions. The compounds according to the invention can thus be employed in the said indications. Above all, however, NO donors have proven suitable for the treatment and prophylaxis of angina pectoris.

The compounds of the general formula I and their pharmacologically acceptable acid addition salts can therefore be administered to humans as medicines on their own, in mixtures with one another or in the form of pharmaceutical preparations which permit enteral or parenteral use and which as active constituents contain an effective dose of at least one compound of the general formula I or of an acid addition salt thereof, in addition to customary pharmaceutically innocuous excipients and additives.

The medicines can be administered orally, for example in the form of pills, tablets, coated tablets, sugar-coated tablets, hard and soft gelatin capsules, solutions, syrups, emulsions or suspensions or aerosol mixtures. However, administration can also be carried out rectally, for example in the form of suppositories, or parenterally, for example in the form of injection solutions, or percutaneously, for example in the form of ointments or tinctures.

For the preparation of the pharmaceutical preparations, pharmaceutically inert inorganic or organic excipients can be used. For the preparation of pills, tablets, sugar-coated tablets and hard gelatin capsules, for example lactose, maize starch or derivatives thereof, talc, stearic acid or its salts, etc., can be used. Excipients for soft gelatin capsules and suppositories are, for example, fats, waxes, semi-solid and liquid polyols, natural or hardened oils etc. Suitable excipients for the preparation of solutions and syrups are, for example, water, sucrose, dextrose, glucose, polyols, etc. Suitable excipients for the preparation of injection solutions are, for example, water, alcohols, glycerol, polyols or vegetable oils.

Besides the active compounds and excipients, the pharmaceutical preparations can additionally contain additives, such as, for example, fillers, extenders, disintegrants, binders, lubricants, wetting agents, stabilisers, emulsifiers, preservatives, sweeteners, colorants, flavourings or aromatisers, buffer substances, and also solvents or solubilisers or agents for achieving a depot effect, and also salts for changing the osmotic pressure, coating agents or antioxidants. They can also contain two or more compounds of the general formula I or their pharmacologically acceptable acid addition salts and additionally other therapeutically active substances.

Other therapeutically active substances of this type are, for example: β-receptor blockers, such as, for example, propranolol, pindolol, metoprolol; vasodilators, such as, for example, carbocromen; tranquillisers, such as, for example, barbituric acid derivatives, 1,4-benzodiazepines and meprobamate; diuretics, such as, for example, chlorothiazide; cardiotonic agents, such as, for example, digitalis preparations; hypotensive agents, such as, for example, hydralazine, dihydralazine, ramipril, prazosine, clonidine, rauwolfia alkaloids; agents which lower the fatty acid level in the blood, such as, for example, bezafibrate, phenofibrate; and agents for thrombosis prophylaxis, such as, for example, phenprocoumon.

The compounds of the general formula I, their pharmacologically acceptable acid addition salts and pharmaceutical preparations which contain the compounds of the general formula I or their pharmacologically acceptable acid addition salts as active compounds can be used in humans in the control or prevention of disorders of the cardiovascular system, for example as antihypertensive medicines in the various forms of high blood pressure, and in the control or prevention of angina pectoris, etc. Moreover, they can also be employed for the treatment of erectile dysfunctions. The dose can vary within wide limits and is to be adjusted to the individual conditions in each individual case. In general, in the case of oral administration a daily dose of about 0.5 to 100 mg, preferably 1 to 20 mg, per human individual is adequate. In the case of other application forms also, the daily dose, on account of the good absorption of the active compounds, lies within similar ranges of amounts, i.e. in general also 0.5 to 100 mg/human. The daily dose is normally divided into several part administrations, for example 2 to 4 part administrations.

PREPARATION EXAMPLES 1. 3-Phenyl-4-(methoxycarbonylmethylmercapto)-1,2,5-oxadiazole-2-oxide A mixture of 4.6 g of 3-phenyl-4-nitrofuroxan, 2.4 g of methyl thioglycolate and 2.2 g of triethylamine in 50 ml of methanol is stirred under a nitrogen atmosphere. In the course of this, the mixture warms to about 40° C. After 1 hour, it is poured into ice-water, whereupon a solid separates after stirring briefly, which is filtered off with suction and recrystallised from isopropanol.

Yield: 3.7 g M.p. 59°–61° C.

2. 3-Phenyl-4-(methoxycarbonylmethylsulphinyl)-1,2,5-oxadiazole-2-oxide 4.4 g of the compound from Example 1 are initially introduced into 17 ml of glacial acetic acid and the mixture is treated with 16 ml of a 35% strength hydrogen peroxide solution. The precipitate which separates is filtered off with suction after 2 days, the mother liquor is diluted with ice-water and the freshly formed precipitate is filtered off with suction. Both solids were recrystallised together from isopropanol.

Yield: 3.9 g M.p. 85°–87° C.

3. 3-Phenyl-4-(aminocarbonylmethylmercapto)-1,2,5-oxadiazole-2-oxide

Gaseous ammonia is passed into a mixture of 4 g of the compound of Example 1 and 50 ml of methanol until it is saturated. After standing at room temperature for 20 hours, the reaction is complete. The precipitate is filtered off with suction and recrystallised from isopropanol.

Yield: 2.4 g M.p. 174°–176° C.

4. 3-Phenyl-4-(2-diethylaminoethylmercapto)-1,2,5-oxadiazole-2-oxide hydrochloride 4.75 g of 2-diethylaminoethyl mercaptan hydrochloride are slowly treated with 3.3 g of a 50% strength sodium hydride in oil suspension in 100 ml of THF under a nitrogen atmosphere. After 1 hour, 5 g of 3-phenyl-4-nitrofuroxan are introduced and the mixture is stirred for 20 hours. The inorganic salts are filtered off with suction and the filtrate is concentrated. The residue is taken up in water and extracted with methylene chloride. After drying and concentrating, the residue is dissolved in ethyl acetate and the product is precipitated by introducing hydrogen chloride and filtered off with suction.

Yield: 4.1 g M.p. 201° C. (dec.)

5. 3-Phenyl-4-(2-diethylaminoethylsulphonyl)-1,2,5-oxadiazole-2-oxide 2 g of the compound from Example 4 are initially introduced into glacial acetic acid (15 ml) and the mixture is treated with 3.4 g of 35% strength hydrogen peroxide. It is stirred for 6 hours and then concentrated. The residual oil is mixed with a little isopropanol and diluted with diisopropyl ether, a precipitate separating which is filtered off with suction.

Yield: 1.4 g M.p. 136°–138° (dec.)

6. 3-Phenyl-4-(2-(N-benzyl-N-methylamino)ethoxy)-1,2,5-oxadiazole-2-oxide hydrochloride A mixture of 2.5 g of 2-(N-benzyl-N-methylamino)ethanol, 0.7 g of 50% strength NaH, 2.5 g of 3-phenyl-4-nitrofuroxan and 30 ml of THF is stirred for 2 hours and then concentrated. The residue is taken up in water and extracted with methylene chloride. After drying and concentrating in a rotary evaporator, the residual oil is dissolved in ethyl acetate and treated with hydrogen chloride. The precipitate which separates is filtered off with suction, washed with ethyl acetate and dried.

Yield: 2.7 g M.p. 163° C. (dec.)

The following were prepared analogously to Examples 1 to 6:

7) 3-Phenyl-4-butylmercapto-1,2,5-oxadiazole-2-oxide M.p.—(oil)

8) 3-Phenyl-4-(2-hydroxyethylmercapto-1,2,5-oxadiazole-2-oxide M.p.—(oil)

9) 3-Phenyl-4-butylsulphonyl-1,2,5-oxadiazole-2-oxide M.p. 79°–81° C.

10) 3-Phenyl-4-(2-hydroxyethylsulphonyl)-1,2,5-oxadiazole-2-oxide M.p. 57°–60° C.

11) 3-Phenyl-4-(2-oxopyrrolidin-1-yl)-1,2,5-oxadiazole-2-oxide M.p. 101°–102° C.

12) 3-Phenyl-4-(pyrid-3-ylmethoxy)-1,2,5-oxadiazole-2-oxide M.p. 110°–112° C.

13) 3-Phenyl-4-(2-methoxyethoxy)-1,2,5-oxadiazole-2-oxide M.p. 39°–41° C.

14) 3-Phenyl-4-(2-diethylaminoethoxy)1,2,5-oxadiazole-2-oxide hydrochloride M.p. 181° C. (dec.)

15) 3-Phenyl-4-(3-dimethylaminopropoxy)-1,2,5-oxadiazole-2-oxide hydrochloride M.p. 167° C. (dec.)

16) S-(3-Phenyl-2-oxo-1,2,5-oxadiazol-4-yl)-N-acetylcysteine M.p. 159°–161° C. (dec.)

17) 3-Phenyl-4-allylmercapto-1,2,5-oxadiazole-2-oxide M.p.—(oil)

18) 3-Phenyl-4-ethylmercapto-1,2,5-oxadiazole-2-oxide M.p.—(oil)
19) 3-Phenyl-4-(aminocarbonylmethylsulphinyl)-1,2,5-oxadiazole-2-oxide M.p. 166°–167° C.
20) 3-Phenyl-4-ethylsulphonyl-1,2,5-oxadiazole-2-oxide M.p. 105°–108° C.
21) 3-Phenyl-4-(phenylmethylmercapto)1,2,5-oxadiazole-2-oxide M.p. 105°–108° C.

The pharmacological action of the compounds of the general formula I was determined by a modified method of Godfraind and Kaba (Arch. Int. Pharmacodyn. Ther. 196, (Suppl) 35 to 49, 1972) and by Schüman et al. (Naunyn-Schmiedeberg's Arch. Pharmacol. 289, 409 to 418, 1975). In this method, spiral strips of the pulmonary artery of the guinea-pig are depolarised using 40 mmol/l potassium after equilibration in calcium-free Tyrode solution. An addition of 0.5 mmol/l of $CaCl_2$ then induces a contraction.

The relaxing effect of the test substance is determined by cumulative addition in ½ log 10 graded concentrations. From the concentration-effect curve (abscissa: -log mol/l of test substance, ordinate: % inhibition of the maximum contraction, average value of 4 to 6 vessel strips), the concentration of the test substance is determined which inhibits the contraction by 50% (=$IC_{50}$, mol/l).

The following values were obtained:

| Compound | $IC_{50}$ (mol/l) |
| --- | --- |
| 2 | $3 \times 10^{-6}$ |
| 5 | $7 \times 10^{-7}$ |
| 6 | $4 \times 10^{-6}$ |
| 9 | $3 \times 10^{-8}$ |
| 10 | $3 \times 10^{-7}$ |
| 12 | $3 \times 10^{-6}$ |
| 19 | $2 \times 10^{-6}$ |
| 20 | $5 \times 10^{-8}$ |
| Molsidomine (comparison) | $3 \times 10^{-4}$ |
| Isosorbide-5-mononitrate (comparison) | $>1 \times 10^{-4}$ |

It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

We claim:
1. Phenylfuroxans of the formula I:

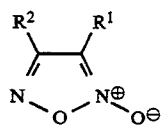

in which one of the radicals $R^1$ and $R^2$ represents phenyl and the other represents

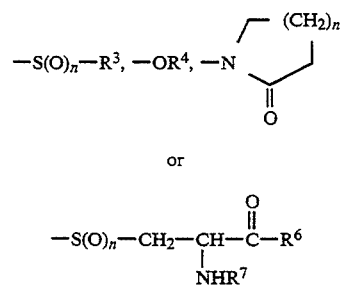

where
$R^3$ denotes $(C_1-C_6)$-alkyl, $(C_5-C_7)$-cycloalkyl, $(C_7-C_{10})$-aralkyl, $(C_3-C_7)$-alkenyl, $-(CH_2)_m R^5$ or $-(CH_2)_n-CO-R^6$;
$R^4$ denotes $(C_3-C_6)$-alkyl, $(C_5-C_7)$-cycloalkyl, $(C_3-C_7)$-alkenyl, $-(CH_2)_n-$ Het, $-(CH_2)_m-R^5$ or $(C_7-C_{10})$-aralkyl;
$R^5$ denotes hydroxyl, $C_1-C_6$-alkoxy, $(C_1-C_6)$-alkylamino, di-$(C_1-C_6)$-alkylamino or $N-(C_1-C_6)$-alkyl-N-benzylamino;
$R^6$ denotes hydroxyl, amino, $(C_1-C_6)$-alkylamino, di-$(C_1-C_6)$-alkyl-amino or $OR^{3'}$, where $R^{3'}$, with the exception of $-(CH_2)_n-CO-R^6$, is defined as $R^3$;
$R^7$ denotes hydrogen, $(C_1-C_6)$-alkyl or $(C_2-C_7)$-alkylcarbonyl;
Het represents a 5- to 7-membered heterocycle containing

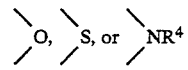

as heteromembers; and
n represents 0, 1 or 2 and
m represents 2, 3 or 4,
and their pharmacologically acceptable acid addition compounds.

2. Phenylfuroxans according to claim 1, characterised in that $R^2$ denotes phenyl and $R^1$ denotes $-S(O)_n-R^3$ or $-OR^4$.

3. Phenylfuroxans according to claim 1, characterised in that $R^1$ denotes phenyl.

4. Phenylfuroxans according to claim 1, characterised in that $R^1$ denotes phenyl and $R^2$ denotes $-S(O)_n-R^3$.

5. Phenylfuroxans according to claim 1, characterised in that $R^1$ denotes phenyl and $R^2$ denotes $-OR^4$.

6. Process for the treatment of disorders of the cardiovascular system, which comprises administering effective amounts of a phenylfuroxan of the formula I according to claim 1, or a pharmacologically acceptable acid addition compound thereof, to a patient in need thereof.

7. Pharmaceutical preparation, characterised in that it contains a phenylfuroxan of the formula I according to claim 1, or a pharmacologically acceptable acid addition compound thereof as active compound, together with pharmaceutically acceptable excipients and additives and, optionally additionally one or more other pharmacological active compounds.

8. Process according to claim 6 in which the disorder being treated is angina pectoris.

9. Process according to claim 6 in which the disorder being treated is erectile dysfunction.

* * * * *